(12) United States Patent
Rabb et al.

(10) Patent No.: US 9,841,344 B2
(45) Date of Patent: Dec. 12, 2017

(54) SYSTEM AND METHODS FOR MONITORING LEAKS IN UNDERGROUND STORAGE TANKS

(71) Applicant: LEAK DETECTION TECHNOLOGIES, INC., Tucson, AZ (US)

(72) Inventors: David M. Rabb, Tucson, AZ (US); Kenneth H. Huey, Tucson, AZ (US)

(73) Assignee: LEAK DETECTION TECHNOLOGIES, INC., Tucson, AZ (US)

( * ) Notice: Subject to any disclaimer, the term of this patent is extended or adjusted under 35 U.S.C. 154(b) by 157 days.

(21) Appl. No.: 15/084,267

(22) Filed: Mar. 29, 2016

(65) Prior Publication Data

US 2017/0322103 A1    Nov. 9, 2017

(51) Int. Cl.
*G01N 1/40* (2006.01)
*G01M 3/20* (2006.01)
(Continued)

(52) U.S. Cl.
CPC ............... *G01M 3/205* (2013.01); *G01N 1/40* (2013.01); *G01N 27/16* (2013.01); *G01N 2030/125* (2013.01)

(58) Field of Classification Search
CPC ........ G01N 1/2214; G01N 1/40; G01N 1/405; G01N 2030/125; G01N 1/02;
(Continued)

(56) References Cited

U.S. PATENT DOCUMENTS

| | | | |
|---|---|---|---|
| 3,247,375 A | 4/1966 | Lovelock | 250/43.5 |
| 3,361,908 A | 1/1968 | Petitjean et al. | 250/43.5 |

(Continued)

FOREIGN PATENT DOCUMENTS

| | | | |
|---|---|---|---|
| CA | 2714125 | 2/2012 | G01M 3/04 |
| WO | WO2008137279 | 11/2008 | G01M 3/22 |

OTHER PUBLICATIONS

Office Action issued in U.S. Appl. No. 14/884,621, dated Jul. 19, 2017 (23 pgs).
(Continued)

*Primary Examiner* — David A Rogers
(74) *Attorney, Agent, or Firm* — Hayes Soloway P.C.

(57) ABSTRACT

Leak detection system and method for monitoring leaks in underground and aboveground storage tanks, pipelines or other containments, including single, double or triple wall containments are provided. A leak detection apparatus includes an oxidation chamber, a chemical marker concentrator, a mass spectrometer (MS) ion trap and a scroll vacuum pump. Vapor samples carrying marker chemicals introduced into a tank, pipeline, or other containment are injected at sample injection point into an oxidation chamber. Oxygen from an oxygen source is fed into oxidation chamber to destroy or oxidize contaminates such as hydrocarbons in the vapor without destroying or oxidizing the chemical markers. Effluent from the oxidation chamber is passed to an elongate conduit with a metal foil or screen suspended within the conduit. The marker chemicals are attracted by a chemical coating on the foil/screen and released by heating the metal. The released marker chemicals are fed into a mass spec ion trap for leakage analysis and results.

20 Claims, 4 Drawing Sheets

(51) Int. Cl.
*G01N 30/12* (2006.01)
*G01N 27/16* (2006.01)

(58) Field of Classification Search
CPC ........... G01N 1/2202; G01N 2030/009; G01N 2030/121; G01N 2030/484; G01N 2030/8405; G01N 21/3504; G01N 27/16
See application file for complete search history.

(56) References Cited

U.S. PATENT DOCUMENTS

| | | | |
|---|---|---|---|
| 3,518,059 A * | 6/1970 | Levy .................... | G01N 30/12 422/78 |
| 3,714,421 A | 1/1973 | Josias et al. ................ | 250/43.5 |
| 4,063,156 A | 12/1977 | Patterson ...................... | 324/33 |
| 4,141,692 A | 2/1979 | Keller ............................. | 44/59 |
| 4,156,813 A | 5/1979 | Flanagan et al. ............ | 250/381 |
| 4,173,141 A | 11/1979 | Kissell et al. ................ | 73/40.7 |
| 4,328,700 A | 5/1982 | Fries ............................ | 73/40.7 |
| 4,551,154 A | 11/1985 | Malcosky et al. ............ | 48/193 |
| 4,593,530 A | 6/1986 | Longsworth ................. | 62/55.5 |
| 4,676,261 A | 6/1987 | Blaul ........................ | 134/104.4 |
| 4,690,689 A | 9/1987 | Malcosky et al. ............ | 48/174 |
| 4,709,577 A | 12/1987 | Thompson ................... | 73/40.7 |
| 4,725,551 A | 2/1988 | Thompson ...................... | 436/3 |
| 4,748,847 A | 6/1988 | Sheahan ....................... | 73/40.7 |
| 4,773,255 A | 9/1988 | Malcosky et al. ............ | 73/40.7 |
| 4,806,314 A * | 2/1989 | Fertig .................... | G01N 27/16 422/78 |
| 4,819,477 A * | 4/1989 | Fisher .................. | G01N 1/2258 73/28.01 |
| 4,896,528 A | 1/1990 | Lewis ........................... | 73/40.7 |
| 5,012,052 A * | 4/1991 | Hayes ............... | G01N 30/7206 250/282 |
| 5,046,353 A | 9/1991 | Thompson ................... | 73/40.7 |
| 5,048,324 A | 9/1991 | Thompson ................... | 73/40.7 |
| 5,070,723 A | 12/1991 | Tsou et al. .................... | 73/40.7 |
| 5,076,728 A | 12/1991 | Golding ........................ | 405/128 |
| 5,092,155 A * | 3/1992 | Rounbehler ............. | G01N 1/02 436/156 |
| 5,111,882 A | 5/1992 | Tang et al. .................... | 166/252 |
| 5,320,967 A | 6/1994 | Avallone et al. .............. | 436/50 |
| 5,388,446 A | 2/1995 | Kronberg ..................... | 73/40.7 |
| 5,409,839 A | 4/1995 | Balestrieri et al. ............ | 436/56 |
| 5,428,988 A * | 7/1995 | Starkovich ............ | B60R 21/264 180/282 |
| 5,447,055 A * | 9/1995 | Thompson ............. | G01M 3/226 73/23.35 |
| 5,767,390 A | 6/1998 | Chapman, IV ............... | 73/40.7 |
| 5,922,943 A | 7/1999 | Chapman, IV ............... | 73/40.7 |
| 5,939,619 A | 8/1999 | Achter et al. ................. | 73/40.7 |
| 6,003,365 A | 12/1999 | Pope et al. ................. | 73/152.39 |
| 6,025,200 A | 2/2000 | Kaish et al. ................... | 436/56 |
| 6,035,701 A | 3/2000 | Lowry et al. ................. | 73/40.7 |
| 6,116,776 A | 9/2000 | Bowling .......................... | 374/4 |
| 6,196,056 B1 | 3/2001 | Ewing et al. ................. | 73/40.7 |
| 6,214,624 B1 | 4/2001 | Barker et al. ................... | 436/8 |
| 6,354,141 B1 | 3/2002 | Pierrejean et al. ........... | 73/40.7 |
| 6,460,405 B1 | 10/2002 | Mayer et al. ................. | 73/40.7 |
| 6,564,614 B1 | 5/2003 | Doris ............................ | 73/49.2 |
| 6,817,227 B2 | 11/2004 | Thompson et al. .......... | 73/40.7 |
| 6,840,086 B2 | 1/2005 | McCoy et al. ................ | 73/40.7 |
| 6,860,141 B2 | 3/2005 | McCoy et al. ................ | 73/40.7 |
| 6,871,556 B2 * | 3/2005 | Andresen .............. | B01L 3/0275 422/429 |
| 6,966,213 B2 | 11/2005 | Hoots et al. .................. | 73/40.7 |
| 7,032,662 B2 | 4/2006 | Malone et al. ............ | 166/252.6 |
| 7,047,830 B2 | 5/2006 | Bratton et al. ............... | 73/865.8 |
| 7,083,742 B2 | 8/2006 | Nimitz et al. ................... | 252/8 |
| 7,140,232 B2 | 11/2006 | Wright et al. ............... | 73/25.01 |
| 7,178,385 B2 | 2/2007 | McCoy et al. ................ | 73/40.7 |
| 7,197,914 B2 | 4/2007 | Maresca, Jr. et al. ......... | 73/40.7 |
| 7,331,248 B2 | 2/2008 | Maresca, Jr. et al. ....... | 73/865.8 |
| 7,576,319 B2 * | 8/2009 | Miller .................. | G01N 27/622 250/281 |
| 8,281,642 B2 * | 10/2012 | Lee ...................... | G01N 27/127 73/23.2 |
| 8,302,461 B2 * | 11/2012 | Angster ............. | G01N 21/1702 73/31.04 |
| 8,448,495 B2 * | 5/2013 | Breviere .................. | G01N 1/40 250/343 |
| 8,756,975 B2 * | 6/2014 | Wu .......................... | G01N 1/14 73/31.05 |
| 8,806,919 B2 * | 8/2014 | Solomon ................. | G01M 3/22 73/40.7 |
| 2003/0082918 A1 * | 5/2003 | Hayasaka .............. | B01D 53/02 438/706 |
| 2004/0170538 A1 * | 9/2004 | Kawakami ............... | B01J 19/10 422/128 |
| 2006/0000298 A1 * | 1/2006 | Thompson ........... | G01N 1/2214 73/863.81 |
| 2013/0025349 A1 * | 1/2013 | Solomon ................. | G01M 3/22 73/40.7 |
| 2017/0184554 A1 * | 6/2017 | Ghiasvand ........... | G01N 30/482 |

OTHER PUBLICATIONS

"Image of garden sprayer for bubble detection fluids". Nondestructive Testing Handbook, vol. 1 (Leak Testing), $2^{nd}$ Edition, American Society for Nondestructive Testing, Inc., 1982, p. 420.

Nelson et al., "Field Study of the Partitioning Tracer Method for Detection of Dense Nonaqueous Phase Liquid in a Trichloroethene-Contaminated Aquifer," Environmental Science & Technology, vol. 30, No. 9, 1996, pp. 2859-2863 (5 pgs).

EPRI, "Condenser Leak Detection by Using $SF_6$ as a Tracer Gas," Technical Brief (undated) (2 pgs).

* cited by examiner

SYSTEM AND METHODS FOR MONITORING LEAKS IN UNDERGROUND STORAGE TANKS

FIELD OF THE DISCLOSURE

The present disclosure is generally related to leak detection system and method, and more particularly is related to system and method for monitoring leaks in aboveground and underground containments such as pipelines, storage tanks and the like.

BACKGROUND OF THE DISCLOSURE

Underground and aboveground containments have been used in various applications, such as in the petroleum, nuclear, and laboratory industry. Those containments need to be monitored for leakage prior to or during usage. Systems for monitoring and detecting the location of leaks in underground storage tanks and pipelines have been described.

U.S. Pat. No. 4,709,577 describes a fluorinated halocarbon compound tracer with a boiling point less than that of gasoline. The tracer is slowly dispensed within the tank. A sampling pipe having a plurality of apertures is buried in selected locations in the vicinity of the tank, and samples of the soil gas are pumped from the pipe and supplied to a Nafion water separator. If a leak in the tank should occur, the tracer will exit with the leaking gasoline, quickly vaporize, and travel rapidly by molecular diffusion. Elements of the tracer will therefore be detected in the soil gas pumped from the sample pipe using standard gas chromatography techniques, indicating that a leak exists in the tank.

U.S. Pat. No. 4,725,551 describes mixing a tracer material such as a fluorinated halocarbon compound with fluids in underground storage tanks. Air drawn down into a vapor pipe passes through the storage tanks and into a sample collection pipe. Any tracer leaked from the tanks will be picked up and drawn into the sample collection pipe. The air in the sample pipe is tested for the presence of the tracer after water vapor is removed from the air sample.

Such prior art detectors typically employ gas chromatographic (GC) device with a chromatographic column and electron capture detector (ECD) equipment which include where chemical markers are injected into a pipe or storage tank and detected when the markers exit the tank as a leak. GC equipment is relatively slow, cumbersome and overelaborate to use. Therefore, there is a need for a method and system for leakage detection for aboveground and underground tanks and containments with improved detection speed and operation simplicity as compared to conventional detection apparatus employing GC methods.

SUMMARY OF THE DISCLOSURE

Embodiments of the present disclosure provide leak detection system and method for monitoring leaks in aboveground and underground storage tanks or containments, single, double or triple wall pipelines and the like. Briefly described, in architecture, one embodiment of a containment leak detection apparatus, among others, can be implemented as follows. A leak detection apparatus comprises an oxidation chamber, a chemical marker concentrator, a mass spectrometer (MS) ion trap and a scroll vacuum pump. Samples are taken in the area surrounding the containment and may have or had hydrocarbon contamination which will affect the efficiency of the MS Ion Trap. Vapor samples taken in the area surrounding the containment where one or more chemical markers has been mixed. The vapor sample is injected at the sample injection point into an oxidation chamber, which is also coupled to an oxygen source. Oxygen from the oxygen source is fed into the oxidation chamber wherein contaminates such as hydrocarbons in the vapor are destroyed or oxidized without destroying the chemical markers.

In one embodiment, the oxidation chamber comprises a solid metal body with a conduit containing a dry chemical through which the vapor is passed, and an imbedded heating element. The heating element permits rapid and controlled heating for the conduit to a desired temperature. By heating the oxidation chamber to a precise predetermined temperature, the dry chemical in an atmosphere of oxygen absorbs and destroys the contaminates while allowing the markers to pass through without being destroyed. This process of destroying the contaminates with little or negligible degradation of the markers allows the mass ion trap to identify the chemical markers with little or no interference in the signal from the contaminates.

Effluent from the oxidation chamber is then passed to a chemical marker concentrator, which comprises an elongate vessel or conduit having an inlet adjacent one end and an outlet adjacent the other end. The outlet is coupled to a vacuum source, such as a scroll vacuum pump. A metal foil or metal screen is suspended within the elongate conduit of chemical marker concentrator. In one embodiment, the metal foil is a metal coated with a chemical coating upon which the chemical marker of interest is attracted to and becomes attach to the coating. The chemical marker of interest is attracted to the chemical absorbent coating on the foil by electrostatic attraction. The foil is connected to an electrical source so that it may be selectively rapidly heated to periodically release the marker compound attracted to the foil. The release period may be pre-determined or dynamically adjusted according to experience. Once all the sample has passed through the chemical marker concentrator and has been capture on the coating the atmosphere in the chemical marker concentrator and mass spec ion trap detector is removed and the chemical marker concentrator is placed under a high vacuum, typically at or below $1\times10^3$ Torr, preferably $1\times10^3$ to $1\times10^{-5}$ Torr, more preferably about $1\times10^{-4}$ Torr. It is preferable that the chemical marker is released rapidly, and essentially at once. The released chemical marker travels through the mass ion trap to evaluate the released marker volume. The chemical coating is selected such that the coating can attract/hold a marker and withstand being placed in a full vacuum, without an early release of the marker(s). In some embodiments, the selective retention of chemical marker compounds through the use of an absorbent material coating bearing the qualities of absorption, include but are not limited to carbon molecular sieve, graphitized carbon black, spherical graphitized polymer carbon, graphitized carbon black and carbon black materials.

After the markers are released from the chemical marker concentrator, the markers arrive at the mass spectrometer (MS) Ion Trap which analyzes for the presence of the marker by determining the molecular weight of the marker compounds.

Accordingly, embodiments provided by this disclosure may advantageously result in improved leakage detection speed and simplified user operation as compared to conventional detection method utilizing a gas chromatography (GC) equipment.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

In the following description, for the purpose of explanation, specific details are set forth in order to provide understanding of the present invention. However, the present invention may be implemented without some of these details. The embodiments of the present invention described below may be incorporated into a number of different means, components, apparatus, circuits and devices. Structures and devices shown in block diagram are illustrative of exemplary embodiments of the present invention. Connections between components may be modified, re-formatted via intermediary components. When the specification makes reference to "one embodiment" or to "an embodiment", it is intended to mean that a particular feature, structure, characteristic, or function described in connection with the embodiment being discussed is included in at least one contemplated embodiment of the present invention. Thus, the appearance of the phrase, "in one embodiment" in different places in the specification does not constitute a plurality of references to a single embodiment of the present invention.

Various embodiments of the invention are used for monitoring leaks in aboveground and underground storage tanks or containments, single, double or triple wall pipelines and the like. Embodiments of the disclosure may take the form of an apparatus or a system comprising multiple apparatus located at different locations. Embodiments of the disclosure, such as a method for monitoring leaks, may also include computer-executable instructions, including algorithms executed by a processor or a programmable computer. Certain aspects of the disclosure can be embodied in a special-purpose computer or data processor that is specifically programmed, configured or constructed to perform one or more of computer-executable instructions described below.

Figure 1:
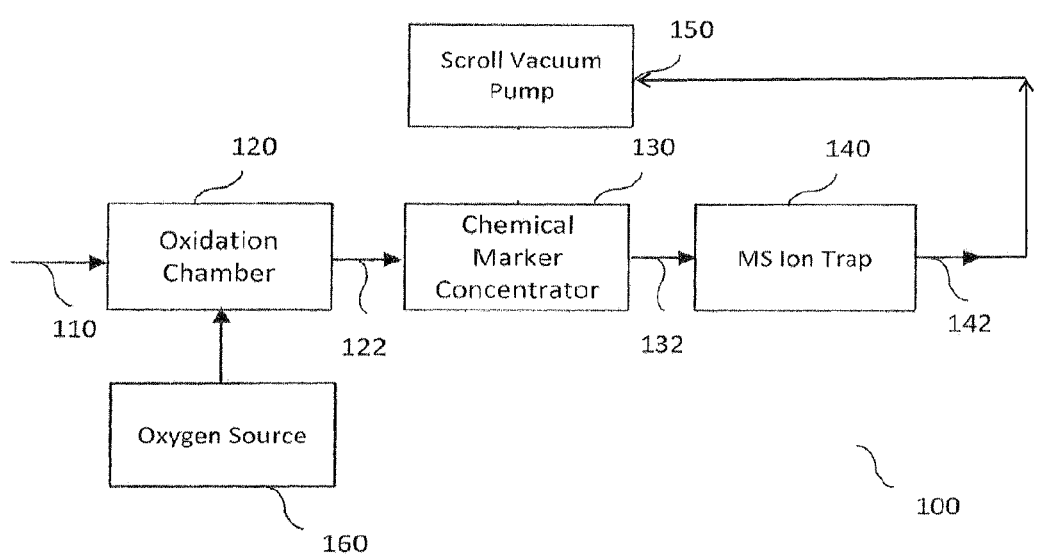
FIG. 1 is a schematic illustration of a leak detection apparatus, in accordance with embodiments of the present disclosure.

FIG. 1 illustrates a schematic illustration of a leak detection apparatus to detect leaks, in accordance with embodiments of the present disclosure. The leak detection apparatus 100 comprises an oxidation chamber 120, a chemical marker concentrator 130, a mass spectrometer (MS) ion trap 140 and a scroll vacuum pump 150. The leak detection apparatus operates as a batch detector. A chemical marker is introduced into the product of a containment. If the containment has a leak the chemical marker will be released into the area surrounding the containment that is being tested. Vapor samples 110 taken from the area surrounding the containment are injected at the sample injection point into an oxidation chamber 120.

In one embodiment, the soil vapor samples 110 may be sourced from an air collection pipe positioned in the vicinity of the underground tank. When the tank is filled with fluid (such as gasoline, diesel, jet fuel, etc.), a chemical marker is added for the purpose of leakage identification. There are circumstances that the fluid vapor itself is not a suitable compound for accurate or reliable leakage detection because ambient environment may also create vapors with similar chemical structure as the fluid vapor (typically hydrocarbons). Subsurface samples taken in areas that have or had hydrocarbon contamination may mask the chemical marker signal within the sample and affect the efficiency of the MS Ion Trap 140. Whenever the underground tank has a leakage, the marker chemical will exit at the leaking spot with the fluid and vaporize quickly. The air collection pipe therefore receives soil vapor with the presence of the marker chemical. Typically, the marker chemical has different chemical analytical signature from the fluid filled within the tank such that the marker chemical vapor may be easily separated from the fluid vapor. For example, when the tank is used to store fuel, the marker chemical may be a halogenated compound, such as a chlorinated halocarbon, fluorinated halocarbon or chlorofluorocarbon.

In one embodiment, the oxidation chamber 120 couples to an oxygen source 160. Oxygen from the regulated oxygen source is fed into oxidation chamber 120 wherein contaminates such as hydrocarbons in the vapor sample are destroyed or oxidized without destroying or oxidizing the chemical markers. The oxygen flow may be regulated automatically via a computer controller mass flow meter for desired or predetermined flow rate and/or time interval.

Figures 2, 3:
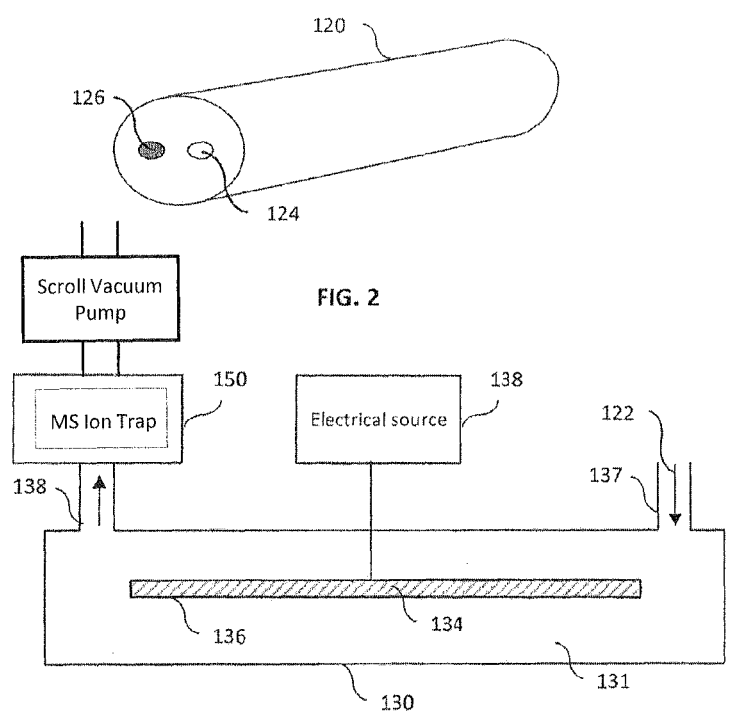
FIG. 2 illustrates an oxidation chamber comprising an elongate conduit and a heating element, in accordance with embodiments of the present disclosure.
FIG. 3 illustrates a metal foil or metal screen suspended within the elongate conduit of the chemical marker concentrator, in accordance with embodiments of the present disclosure.

FIG. 2 illustrates an oxidation chamber 120 comprising an elongate conduit 124 and an imbedded heating element 126 in accordance with embodiments of the present disclosure. In one embodiment, the conduit 124 contains a dry chemical such as palladium, rhodium or platinum through which the vapor is passed. The heating element permits rapid and controlled heating for the conduit to a desired temperature. By heating the oxidation chamber to a predetermined temperature, typically 300 to 350° C., more typically 320 to 340° C., the dry chemical in an atmosphere of oxygen absorbs and destroys the contaminates at a desired or enhanced reaction rate while allowing the markers to pass through without being destroyed. This process of destroying the contaminates with little or negligible degradation of the marker chemicals allows the mass ion trap to identify the chemical markers with little or no interference in signal from the contaminates.

FIG. 3 illustrates a metal foil or metal screen suspended within the elongate conduit of the chemical marker concentrator, in accordance with embodiments of the present disclosure. Effluent 122 from the oxidation chamber is fed into a chemical marker concentrator 130, which comprises an elongate vessel or conduit 131 having an inlet 137 adjacent one end and an outlet 138 adjacent the other end and coupled to a vacuum source 150, such as a scroll vacuum pump. A metal foil 134 is suspended within the elongate conduit 131 of chemical marker concentrator 130. In one embodiment, the metal foil is coated with a chemical coating 136 upon which the chemical marker of interest is collected. The marker chemical is attracted to the chemical coating 136 on the foil by electrostatic attraction. The chemical coating is selected such that the coating can attract/hold a marker and survive being placed in a full vacuum, without an early release of the marker(s). In some embodiments, the chemical coating is absorbent material which offers a selective retention to the chemical marker compounds through the use of a coating bearing the qualities of sorption, include but are not limited to carbon molecular sieve, graphitized carbon black, spherical graphitized polymer carbon, graphitized carbon black and carbon black materials.

In yet another embodiment, the metal foil or metal screen 134 is connected to an electrical source 138 such that it may be rapidly heated to periodically release the marker compound taken up on the foil. Preferably, the attracted chemical marker is released rapidly, and entirely. The electrical source 138 may also be controlled automatically through one or more microprocessor for preset heating interval, temperature, etc. The released chemical marker 132 is fed into the mass ion trap 140 for evaluation. The mass ion trap is utilized with the chemical marker concentrator 130 placed in a low pressure atmosphere environment. For example, the scroll vacuum pump 150 may operate to maintain a predetermined vacuum degree, preferably at or below $1 \times 10^{-3}$ Torr for the chemical marker concentrator 130.

After being released from the chemical marker concentrator, the marker chemicals will make its way to the mass spectrometer (MS) Ion Trap 140 where the marker will be detected and identified by molecular weight and quantified by concentration of the compound. The MS Ion Trap utilizes electric and/or magnetic fields to capture charged particles in an environment isolated from an external environment for mass spectrometry. Depending on the chemical marker used the MS Ion Trap may incorporate a Penning trap (Fourier transform ion cyclotron resonance), Paul trap or Kingdon trap, Quadrupole Ion Trap, or a Triple Quadrupole Trap for capture of charged particles. The MS Ion Trap 140 may couple to the scroll vacuum pump 150 or an independent vacuum pump for maintaining a low pressure atmosphere operation environment.

Figure 4:
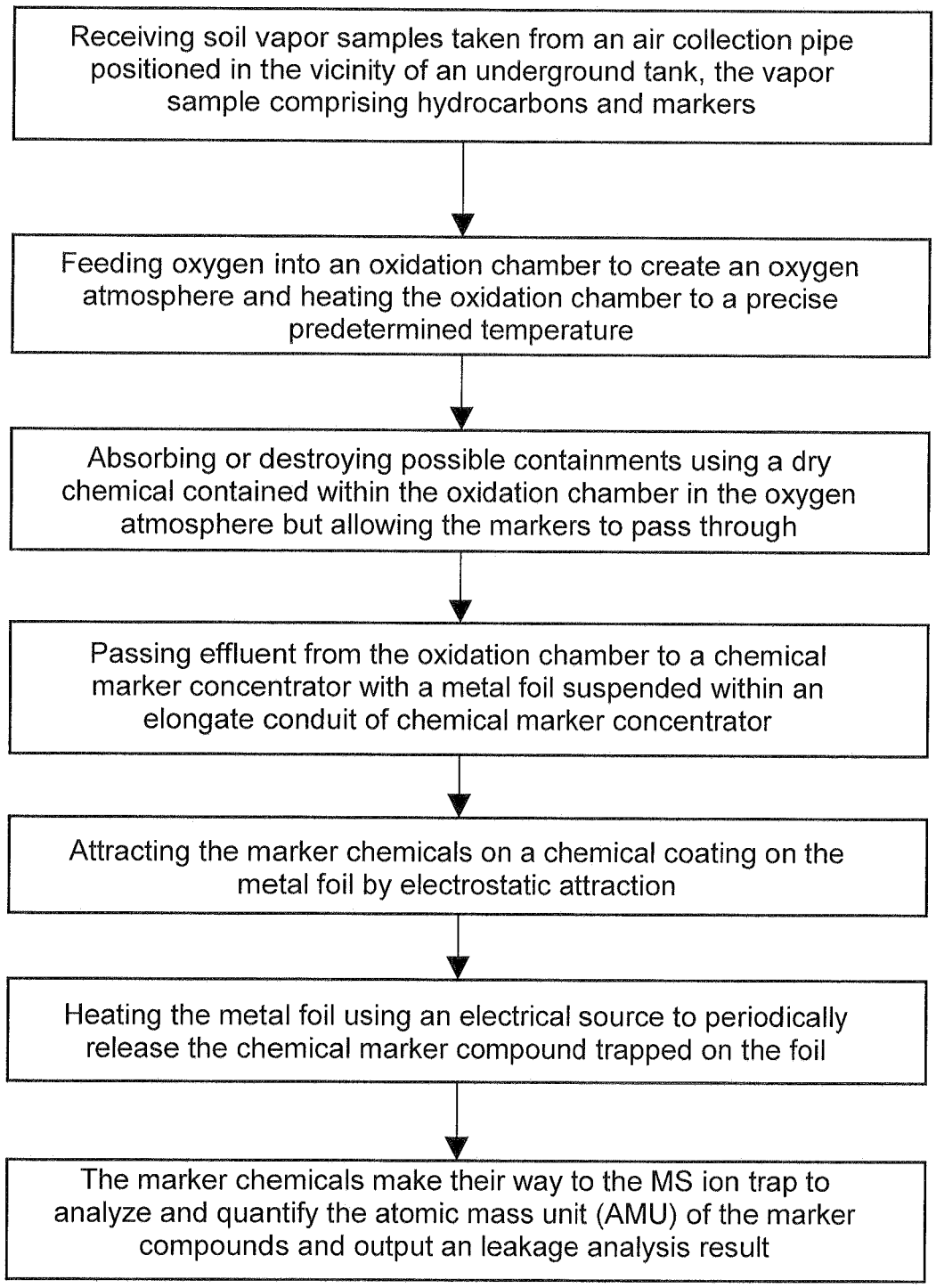
FIG. 4 illustrates the steps for monitoring leaks in underground storage tanks and the like, in accordance with embodiments of the present disclosure.

FIG. 4 illustrates the steps for monitoring leaks in underground storage tanks and the like, in accordance with embodiments of the present disclosure. At step 410, vapor samples are taken from the area surrounding the containment where the chemical marker labeled product resides. Additionally, samples can be taken from an air collection pipe positioned in the vicinity of an underground tank or pipeline containment. Samples are transported to the oxidation chamber where they are injected into the flow stream. The vapor sample may comprise of a variety of contaminates and/or products from the containment such as hydrocarbons and marker chemicals spilling out of the containment through a leak within the underground tank or containment. At step 420, oxygen is fed into the oxidation chamber to create an oxygen atmosphere and the oxidation chamber is heated to a precise predetermined temperature. At step 430, the contaminates are absorbed or destroyed using a dry chemical contained within the oxidation chamber in the oxygen atmosphere. The marker chemicals have little or no negligible degradation when passing through the dry chemicals. At step 440, effluent from the oxidation chamber is passed to an elongate conduit within a chemical marker concentrator with a metal foil or metal screen suspended within the elongate conduit. The metal foil has a chemical coating to attract the marker chemicals by electrostatic attraction, interstitial or chemical bonding during step 450. At step 460, the metal foil is heated using an electrical source to periodically release the marker chemicals attracted on the metal foil. At step 470, the released chemicals are fed into a MS ion trap to analyze for the presence of the marker chemicals by measuring for their molecular weight for each chemical marker. A detection of the marker compounds found in the sample would indicate a leaky containment. The concentration of the marker would quantitate the size (leak rate) of the leak within the containment.

It shall be noted that the above steps for monitoring leaks are performed under specific conditions using a specific embodiment or embodiments. Accordingly, neither these steps nor their results shall be used to limit the scope of the disclosure. Furthermore, it shall be noted that the method for monitoring leaks for underground tanks may be implemented by performing certain steps optionally, extra steps beyond the illustration of FIG. 4, performing certain steps in different orders, and /or performing certain steps concurrently.

Figure 5:
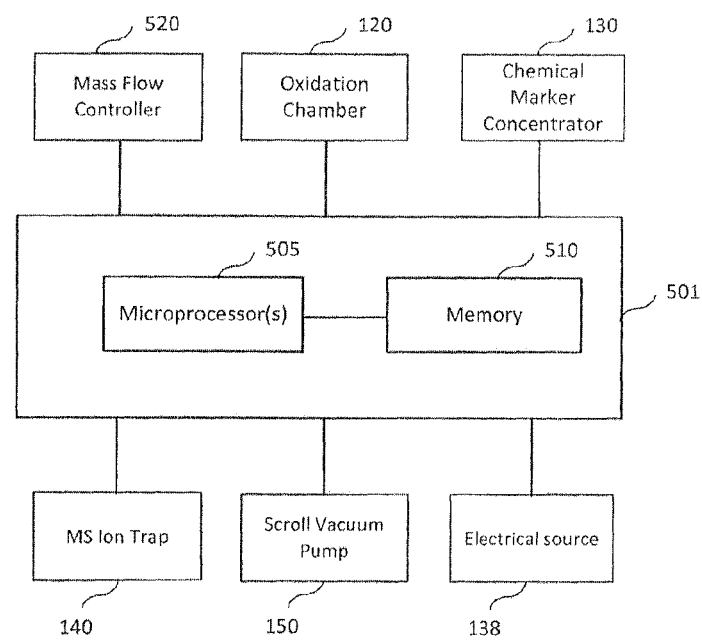
FIG. 5 illustrates a simplified block diagram of a leakage detection system for the implementation of leak monitoring for underground storage tanks according to embodiments of the present disclosure.

FIG. 5 illustrates a simplified block diagram of a leakage detection system for the implementation of leak monitoring for underground or aboveground storage containments according to embodiments of the present disclosure. It will be understood that the functionalities shown for system 500 may operate to support various embodiments. As illustrated in FIG. 5, system 500 includes one or more microprocessors 505 that provide information processing and process controls. The microprocessors 505 may be implemented with a CPU, PLC or the like, and may also include one or more floating point processors for mathematical computations. System 500 also includes a memory 510, which may be in the form of random-access memory (RAM), read-only memory (ROM), or both. The microprocessors 505 and the memory 510. Embodiments of the present invention may be encoded upon one or more non-transitory computer-readable media with instructions stored within the memory 510 for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. The memory 510 may refer as a memory module within a centralized computer 501 or a collection of memory modules placed at different locations or within separate apparatus.

In some embodiments, the centralized computer 501 couples to the oxidation chamber 120, the chemical marker concentrator 130, the mass spectrometer (MS) ion trap 140, the scroll vacuum pump 150, a mass flow controller 520 (or similar controllable valve for controlling oxygen flow from the oxygen source 160), and the electrical source 138 for heating the metal foil 134 via one or more I/O interfaces. The centralized computer 501 controls and coordinates operation parameters for each of the abovementioned components for the implementation of leak monitoring for underground and aboveground storage tanks and containments.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

The invention claimed is:

1. A method for monitoring leaks in underground or aboveground containments, the method comprising:
   receiving at an oxidation chamber vapor samples taken from the area surrounding an underground or aboveground containment or from an air collection pipe positioned in a vicinity of underground tanks or containments, wherein said vapor sample may contain hydrocarbon and other contaminates and marker chemicals added within the underground or aboveground containment;
   feeding oxygen into the oxidation chamber to create an oxygen atmosphere to absorb or destroy contaminates within the vapor samples;
   passing effluent from the oxidation chamber to a chemical marker concentrator with a metal foil or metal screen suspended within an elongate conduit of chemical marker concentrator, the metal foil having a chemical coating to attract and hold the marker chemicals;
   heating the metal foil to release the marker compound attracted on the foil; and
   feeding the released marker chemicals into a mass spectrometer (MS) ion trap to analyze for the presence of the marker chemicals and output a leakage analysis result.

2. The method of claim 1 wherein the oxidation chamber further comprises a dry chemical to absorb or destroy the hydrocarbon contaminates or other products leaked from the containment.

3. The method of claim 2 wherein the dry chemical is selected from the group consisting of palladium, platinum and rhodium.

4. The method of claim 2 wherein the chemical coating is selected from the group consisting of carbon molecular sieve, graphitized carbon black, spherical graphitized polymer carbon, graphitized carbon black, and carbon black material.

5. The method of claim 1 wherein the oxidation chamber is heated to a predetermined temperature by a heating element.

6. The method of claim 1 wherein the metal foil or metal screen is made of steel.

7. The method of claim 1 wherein the marker chemicals are halogenated compounds.

8. The method of claim 1 wherein the chemical marker concentrator is coupled to a vacuum pump to maintain low atmosphere environment.

9. The method of claim 1 wherein the vacuum pump is a scroll vacuum pump.

10. An apparatus for monitoring leaks in aboveground and underground storage tanks and pipeline containments, the apparatus comprising:
    an oxidation chamber to receive vapor samples taken from an area surrounding the containment or samples taken from an air collection pipe positioned in vicinity of the containment, wherein the vapor sample may contain hydrocarbon or other contaminates and marker chemicals added to the containment, the hydrocarbons being absorbed or destroyed within the vapor samples;
    a chemical marker concentrator to receive effluent from the oxidation chamber, the chemical marker concentrator comprising an elongate conduit with a metal foil suspended within the conduit, the metal foil having a chemical coating to attract the marker chemicals, the metal foil being heated to periodically release the marker chemicals attracted on the foil; and
    a mass spectrometer (MS) ion trap to receive the released marker chemicals to analyze for the presence of the marker chemicals by measuring for their molecular weight for each chemical marker and to determine an amount of the marker chemicals and output an leakage analysis result.

11. The apparatus of claim 10 wherein the oxidation chamber further comprises a dry chemical to absorb or destroy hydrocarbons.

12. The apparatus of claim 10 wherein the dry chemical is selected from the group consisting of palladium, rhodium and platinum.

13. The apparatus of claim 10 wherein the oxidation chamber further comprises a heating element to a predetermined temperature.

14. The apparatus of claim 10 wherein the chemical marker concentrator is a metal foil or metal screen.

15. The apparatus of claim 10 wherein the marker chemicals are halogenated compounds.

16. The apparatus of claim 10 wherein the chemical marker concentrator is coupled to a vacuum pump to maintain a vacuum operation environment.

17. The apparatus of claim 16 wherein the vacuum pump is a scroll vacuum pump.

18. A non-transitory computer-readable medium or media comprising one or more sequences of instructions which, when executed by one or more microprocessors, causes the steps to be performed comprising:
    receiving at an oxidation chamber vapor samples taken from an air collection pipe positioned in vicinity of an underground or aboveground containment, wherein the vapor sample may contain hydrocarbon and other contaminates and marker chemicals added to the containment;
    feeding oxygen into the oxidation chamber at a predetermined flow rate to create an oxygen atmosphere and heating the oxidation chamber at a predetermined temperature to absorb or destroy the hydrocarbon contaminates within the vapor samples;
    passing effluent from the oxidation chamber to a chemical marker concentrator with a metal foil or metal screen suspended within an elongate conduit of chemical marker concentrator, the metal foil having a chemical coating to attract and hold the marker chemicals and being heated to periodically release the marker compound attracted on the foil with a predetermined period; and
    receiving the released marker chemicals at a mass spectrometer (MS) ion trap to analyze for the presence of the marker chemicals by measuring for their molecular weight for each chemical marker output an leakage analysis result.

19. The non-transitory computer-readable medium or media of claim 18 wherein the oxidation chamber comprises a dry chemical to absorb or destroy the hydrocarbons.

20. The non-transitory computer-readable medium or media of claim 18 wherein the chemical marker concentrator is coupled to a vacuum pump to maintain a predetermined vacuum degree.

* * * * *